(12) United States Patent
Buder

(10) Patent No.: US 8,128,950 B2
(45) Date of Patent: Mar. 6, 2012

(54) PAPER PRODUCT WITH DISINFECTING PROPERTIES

(75) Inventor: Philip Buder, Ontario (CA)

(73) Assignee: Kruger Products L.P., Mississauga, ON ( * ) Notice: Subject to any disclaimer, the term of this patent is extended or adjusted under 35 U.S.C. 154(b) by 1684 days.

(21) Appl. No.: 10/367,919

(22) Filed: Feb. 19, 2003

(65) Prior Publication Data

US 2004/0161450 A1    Aug. 19, 2004

(51) Int. Cl.
*A01N 25/34* (2006.01)
*A01N 27/00* (2006.01)
*A61K 8/02* (2006.01)
*A61K 31/74* (2006.01)
*C07C 39/12* (2006.01)

(52) U.S. Cl. ..... 424/414; 424/401; 424/402; 424/78.03; 514/844; 514/845; 514/846; 514/847; 514/848; 514/764; 568/747

(58) Field of Classification Search ................... 424/402, 424/404, 405; 428/154; 560/128; 442/61
See application file for complete search history.

(56) References Cited

U.S. PATENT DOCUMENTS

| | | | |
|---|---|---|---|
| 6,133,166 A * | 10/2000 | Nissing et al. | 442/61 |
| 6,238,682 B1 * | 5/2001 | Klofta et al. | 424/402 |
| 6,258,368 B1 * | 7/2001 | Beerse et al. | 424/404 |
| 6,294,186 B1 * | 9/2001 | Beerse et al. | 424/405 |
| 6,325,969 B1 | 12/2001 | Aamodt et al. | |
| 6,399,560 B1 * | 6/2002 | Kwon et al. | 510/382 |
| 6,569,229 B1 * | 5/2003 | Buri et al. | 106/15.05 |

FOREIGN PATENT DOCUMENTS

CA       2023287       2/1991

(Continued)

*Primary Examiner* — Robert A Wax
*Assistant Examiner* — Jeffrey T Palenik

(57) ABSTRACT

A paper product having an antimicrobial composition dispersed with the substrate is provided. In particular, a paper towel such as those found in public washrooms or institutions comprises an antimicrobial composition. The substrate can also be a facial tissue, kitchen towel, serviette or any type of personal hygeine product. The antimicrobial composition preferably comprises a phenol-derived antimicrobial agent. The paper products of the present invention appear dry to the touch.

20 Claims, 5 Drawing Sheets

FOREIGN PATENT DOCUMENTS

| | | |
|---|---|---|
| CA | 2355684 | 6/1999 |
| CA | 2322506 | 9/1999 |
| CA | 2208068 | 11/2000 |
| EP | 0 875 233 * | 4/1998 |
| EP | 0 875 233 A1 * | 4/1998 |
| EP | 0875233 * | 4/1998 |

* cited by examiner

DOSE RESPONSE FOR TARGET FORMULA,
Efficacy To Kill Salmonella choleraesius After Five
(5) Minutes Contact With ABT In Vitro.

FIG. 7

PAPER PRODUCT WITH DISINFECTING PROPERTIES

FIELD OF THE INVENTION

The present invention relates to paper products containing an antimicrobial composition, particularly paper hand towels.

BACKGROUND OF THE INVENTION

Various types of microorganisms can have deleterious effects on human health. Microorganisms are involved in soil and water contamination, food poisoning, skin infections, respiratory infections, bacteremia and viremia. It is well known that contaminated hands can spread many infections. For example, one can be exposed to the common cold from shaking hands with someone who has just sneezed. Furthermore, diseases such as hepatitis can be spread to large numbers of people by an infected individual handling food.

It is also well known that hand washing can remove many microbes and it is recommended that people wash their hands frequently to prevent the spread of disease. In certain environments, such as in food handling and in hospitals, there are strict hand-washing regulations. While washing with soap may decrease the number of microorganisms on the hands, the primary action of plain soap is the mechanical removal of viable transient microorganisms. The effectiveness depends on the thoroughness of the washing. In addition, the water itself may contain water-borne microbes or the hands can become re-contaminated by touching the tap or door handle.

Soap with water can physically remove a certain level of microbes, but antiseptic agents are necessary to kill or inhibit microorganisms and reduce the level still further. There is an increasing public awareness of the health issues surrounding microbial contamination and thus there is an increasing market demand for antimicrobial products. Some examples of antimicrobial products include antibacterial hand soap, surgical disinfectants, household kitchen and bathroom cleansers, diaper wipes, deodorant, facial washcloths, hand wipes and other types of personal hygiene products.

U.S. Pat. No. 6,258,368 is directed to an antimicrobial wipe comprising an absorbent sheet impregnated with an antimicrobial cleansing composition. The composition is pH adjusted in order to be less harsh on the skin and to have a residual antimicrobial effect. The product is formatted as a wet wipe and it is necessary to maintain the moistness for efficacy.

U.S. Pat. No. 6,399,560 is directed to a biocidal composition and a cloth incorporating the composition. The cleaning device is designed to be effective against a wide range of bacteria without being unduly toxic. The biocidal composition requires the addition of a metal pyridinethione.

Canadian Patent No. 2,208,068 discloses a medicated tissue paper product that carries a lotion for soothing irritated and sore nasal areas and a medicinal substance that is either dispersed directly in the lotion or is contained in microcapsules that are dispersed in the lotion. The paper product does not have antimicrobial properties.

U.S. Pat. No. 6,325,969 discloses a paper product impregnated with a volatile biocidal chemical to create a no-growth zone on the paper. The treated paper is not useful as an antimicrobial device.

Many of the commercially available disinfectants have high levels of alcohol or harsh surfactants that tend to dry out and irritate the skin. In addition, wet wipes require special sealable packaging to prevent drying out which would result in a decrease in activity. Drying techniques also affect the efficacy of hand washing protocols. For example, it usually takes longer to dry hands with an air-dryer and people often do not take sufficient time to properly dry the hands. The primary problem with hand hygiene is not a lack of antimicrobial products, but rather a lack of compliance with required standards. A number of studies have looked at the influence of a variety of factors on hand washing behaviour.

Thus, there remains a real and unmet need for an effective and easy-to-use sanitizing aid to help reduce microbial contamination.

SUMMARY OF THE INVENTION

It is an object of the present invention to provide a sanitizing product that is safe and efficacious and does not require airtight packaging.

The present invention provides antimicrobial paper products that are essentially dry. An antimicrobial-containing composition is specially formulated so that it can be applied to a paper product. The antimicrobial has activity in the dry state and its activity is enhanced when it is liberated from the paper product by contact with a fluid.

In one aspect of the invention a substantially dry-to-the-touch paper product is provided. The paper product comprises an antimicrobial active agent dispersed on a support matrix. The antimicrobial agent may be provided in a composition comprising a solubilizing agent. The antimicrobial composition may also include a carrier to enhance application to the matrix. The antimicrobial active agent is generally a bacteriostatic or bacteriocidal agent, a virucide, a fungicide or a disinfectant and is preferably a phenol derivative. Exemplary phenol derivatives include 2-phenylphenol, sodium-2-phenylphenolate, hexachlorophene, chlorhexidine and diphenyl ethers.

In a preferred embodiment, the paper product is a paper hand towel comprising a phenol-derived antimicrobial active agent on a substrate.

The antimicrobial active agent is typically dissolved in a solvent, such as methanol, ethanol, ethylene glycol, isopropanol, polyglycol and propylene glycol to provide an antimicrobial composition.

In a preferred embodiment, the antimicrobial composition comprises 5 to 95% by weight of a phenol-derived antimicrobial agent and 5 to 95% by weight of a solvent, preferably 5-50% of each.

The antimocrobial composition may also include a carrier to facilitate transfer to the paper. A preferred carrier is polyethylene glycol (PEG).

The paper product of the present invention may include an additional component, such as a surfactant, an alcohol, an ether, an emollient, or a fragrance.

In another aspect of the invention, the paper product is an antimicrobial hand towel that comprises a substrate and a phenol-derived antimicrobial active agent disposed on the substrate.

The hand towel may be provided in a format for use in an institutional environment or for use in a consumer environment. When the towel is used to dry the hands, the antimicrobial is transferred onto the hands and can reduce the microbial load on the hands.

The present invention also provides a process for sanitizing hands comprising washing the hands and drying them with the antimicrobial hand towel.

An antimicrobial composition for use on a paper towel is also provided. The composition comprises a phenol-derived antimicrobial agent and a solvent.

A phenol-derived antimicrobial composition can be applied to a paper web using a variety of techniques. For example, spraying, flexographic printing or roto gravure printing techniques can be used.

BRIEF DESCRIPTION OF THE DRAWINGS

The invention is described in more detail herein with reference to the drawings, in which:

FIG. 7 is a graph indicating antimicrobial efficacy at 5 minutes.

DETAILED DESCRIPTION

Figure 1A:
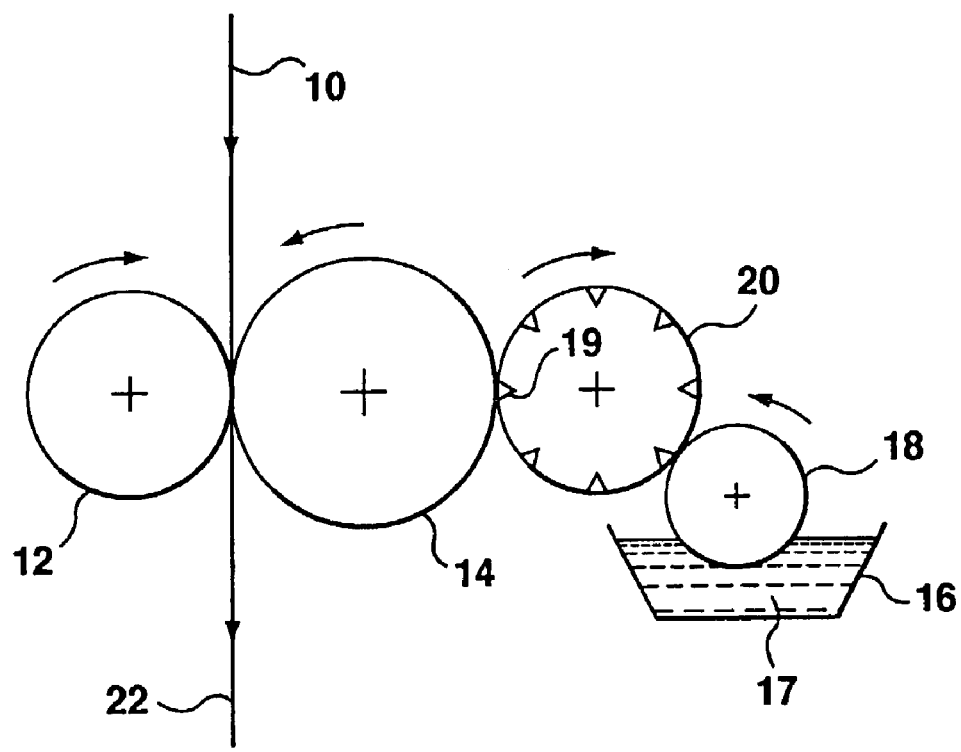
FIGS. 1a and 1b are schematics of flexographic printing systems.

The antimicrobial paper products of the present invention comprise a paper substrate and an antimicrobial active component.

As used herein, the terms "paper" and "substrate" are used interchangeably to refer to sheet material made from all natural filrous materials or a blend of natural and synthetic and/or semi-synthetic fibrous materials. Examples of sheet material include institutional paper hand towels, napkins, serviettes, facial tissue paper, toilet paper, household paper towels and the like.

The paper substrate of the present invention can be prepared using conventional methods. For example, a non-woven substrate comprising filamentous fibers having a web structure can be used. A substrate having a random distribution can also be used. In general, any standard substrate can be used as long as it has an appropriate tensile strength and absorbency. Useful substrates for the practice of the invention typically have a basis weight in the range of about 8 to about 30 pounds per ream and total water absorption capacity of approximately 90 to 400 grams per square meter.

The term "antimicrobial" refers to a biocidal or biostatic compound which controls the viability and/or proliferation of microorganisms. The antimicrobial composition is active against bacteria, mould, fungi and/or yeast. The antimicrobial composition can also be formulated to have a virucidal effect. The antimicrobial agent may be referred to as an anti-bacterial, an anti-mycotic, a virucide, a fungicide, a sanitizer, a disinfectant, a biocide or the like. The antimicrobial agent may be biologically or chemically derived. The antimicrobial agent is preferably provided in an antimicrobial composition which can be applied to the substrate. The term "sanitize" is used broadly herein to refer to a reduction in microbes and not necessarily complete sterilization.

The antimicrobial composition of the present invention comprises a solvent and an antimicrobial active agent. The composition may optionally include a surfactant and/or an additional carrier.

The antimicrobial composition comprises from about 5% to about 95%, preferably 15% to 40% by weight of the antimicrobial active agent. Antimicrobials that are useful in thepresent invention include phenol and phenol derivatives. Some exemplary antimicrobial agents are 2-phenylphenol, sodium-2-phenylphenolate, hexachlorophene, chlorhexidine, diphenyl ethers, etc. A preferred antimicrobial is 2-phenylphenol. The hydrated sodium salt, sodium 2-phenylphenolate and other types of phenol derivatives may also be used. Some exemplary derivatives are available from Bayer under the trademark Preventol™. It is clearly apparent that other antimicrobials having the same properties in terms of biocidal activity and solubility could also be used. The phenol derivatives useful in the present invention have low toxicity and good biodegradability.

The antimicrobial active component is dispersed in a solvent medium or system to solubilize the active ingredients. Preferred solvents are alcohol or ether based and the solvent system is preferably compatible with water. Some examples of solvents include, but are not limited to, methanol, ethanol, ethylene glycol, isopropanol, polyglycol, propylene glycol and mixtures thereof. In a preferred embodiment, a glycol solvent system is used. One preferred solvent is propylene glycol, but it is clearly apparent that any other solvent, which is compatible with application to paper (i.e. not highly volatile, low % water) and which is safe for use by humans, can be used.

A carrier may be added to improve the consistency of the composition. The composition may include polyethylene glycol (PEG) as an extender or co-solvent. The PEG provides added viscosity and is water compatible and facilitates the transfer of the composition to the paper.

The selected antimicrobial is formulated into a composition that provides for a substantially "dry" paper product. In other words, the paper feels more like a dry paper towel than a wet wipe.

The antimicrobial compositions of the present invention are formulated to be compatible with dry paper. It is well known that chemical compositions can be added at the wet end of the paper making process. However, when this is done, expensive additives may be may lost in the white water drained from the paper and treatment of the waste effluent may be required prior to environmental release. On the other hand, the water in aqueous compositions applied at the dry end of the process can have detrimental effects on the strength and flexibility of the paper product. The compositions of the present application are formulated so that they can be added at the dry end of the process without any significant detrimental effects. This extends the application of the composition to grades of paper that would not normally be conducive to the addition of a water-based composition at the dry end. Addition of the composition at the dry end also minimizes waste and provides for a more cost-effective use of the antimicrobial. The resultant antimicrobial paper products feel essentially dry to the touch. The active ingredient of the antimicrobial composition is stable in the dry state and thus the "dry" product has a long shelf life. The antimicrobial is released primarily when the product is wetted.

The antimicrobial composition can be applied to the paper product using various standard techniques such as flexographic printing, spraying or roto gravure printing.

Figure 1B:
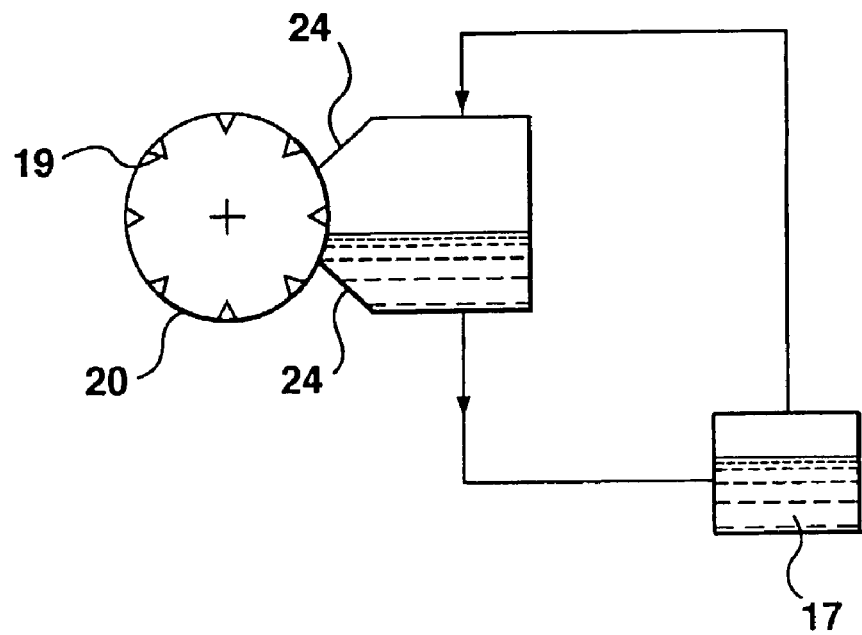

FIGS. 1a and 1b generally illustrate the process of applying the antimicrobial composition to a substrate by a flexographic press. In FIG. 1a, a plain web of paper 10 is fed between a backing roll 12 and plate roll 14 which counter rotate. The antimicrobial composition 17 is placed in a fountain or ink pan 16 and is picked up by the pick up roll 18 and then transferred to the anilox roll or cylinder 20. The anilox roll has engravures or etchings 19 so as to transfer the composition to the plate roll 14 to coat the web 10. The printed web 22 is then rolled, cut and/or folded according to the desired format.

A variation of the flexographic press system is illustrated in FIG. 1*b*. The system comprises a closed cavity system with doctor blades 24 to control the amount of antimicrobial applied to the substrate. Although FIG. 1 illustrates the disinfecting composition being applied to one side of the web, it is clearly apparent that both sides of the web may be coated.

Variations in flexographic printing techniques are contemplated. For example a flexographic press with an "all over" coating roller may be used to apply the composition using standard techniques.

Figure 2:
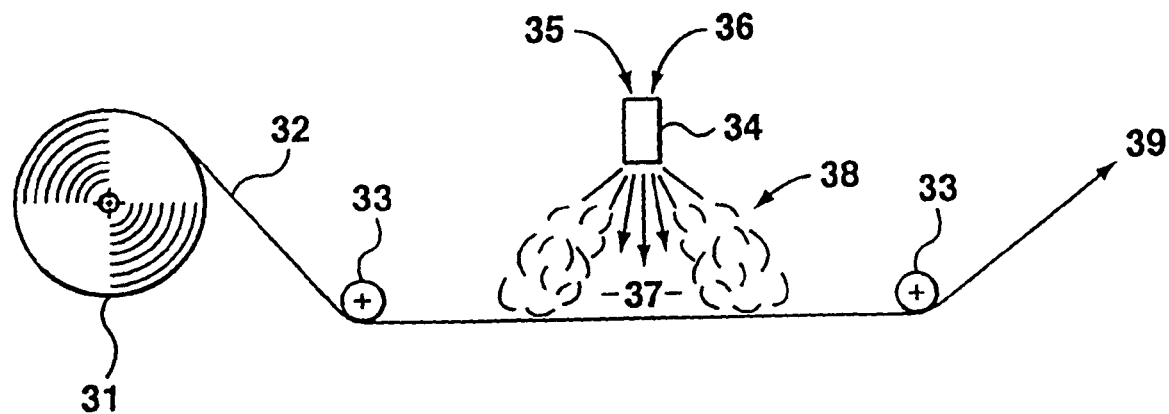
FIG. 2 is a schematic illustrating a spray application method.

FIG. 2 illustrates how the antimicrobial composition can be applied using a spray technique. In the illustration, a roll 31 is comprised of a single ply substrate 32, but it clearly apparent that a multi-ply substrate could also be used. Idler rollers 33 help to keep tension on the substrate web. The antimicrobial solution 35 is mixed with air 36 in a spray nozzle 34 and then applied as an aerated solution 37 to the substrate. The antimicrobial-coated web of paper 39 leaves the spraying zone and proceeds to the next operation (e.g. drying unit, folder, etc.). If the antimicrobial composition is to be sprayed, appropriate containment measures must be taken to address health and safety issues. For example, a closed system could be used.

Figure 3:
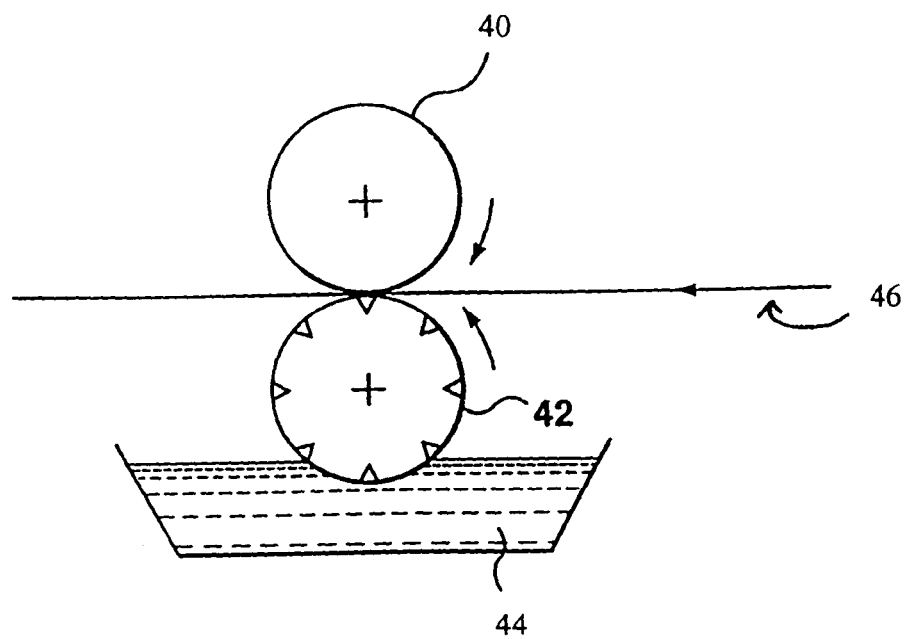
FIG. 3 is a schematic illustrating a roto gravure printing system.

FIG. 3 illustrates schematically a roto gravure press having a backing roll 40, such as a rubber impression roll. The press also includes a gravure roll 42 which contacts the antimicrobial composition 44. This interaction coats the underside 46 of the web.

In addition to the techniques illustrated in FIGS. 1, 2 and 3, the paper product of the present invention can be prepared using other standard paper production techniques.

Figure 4:
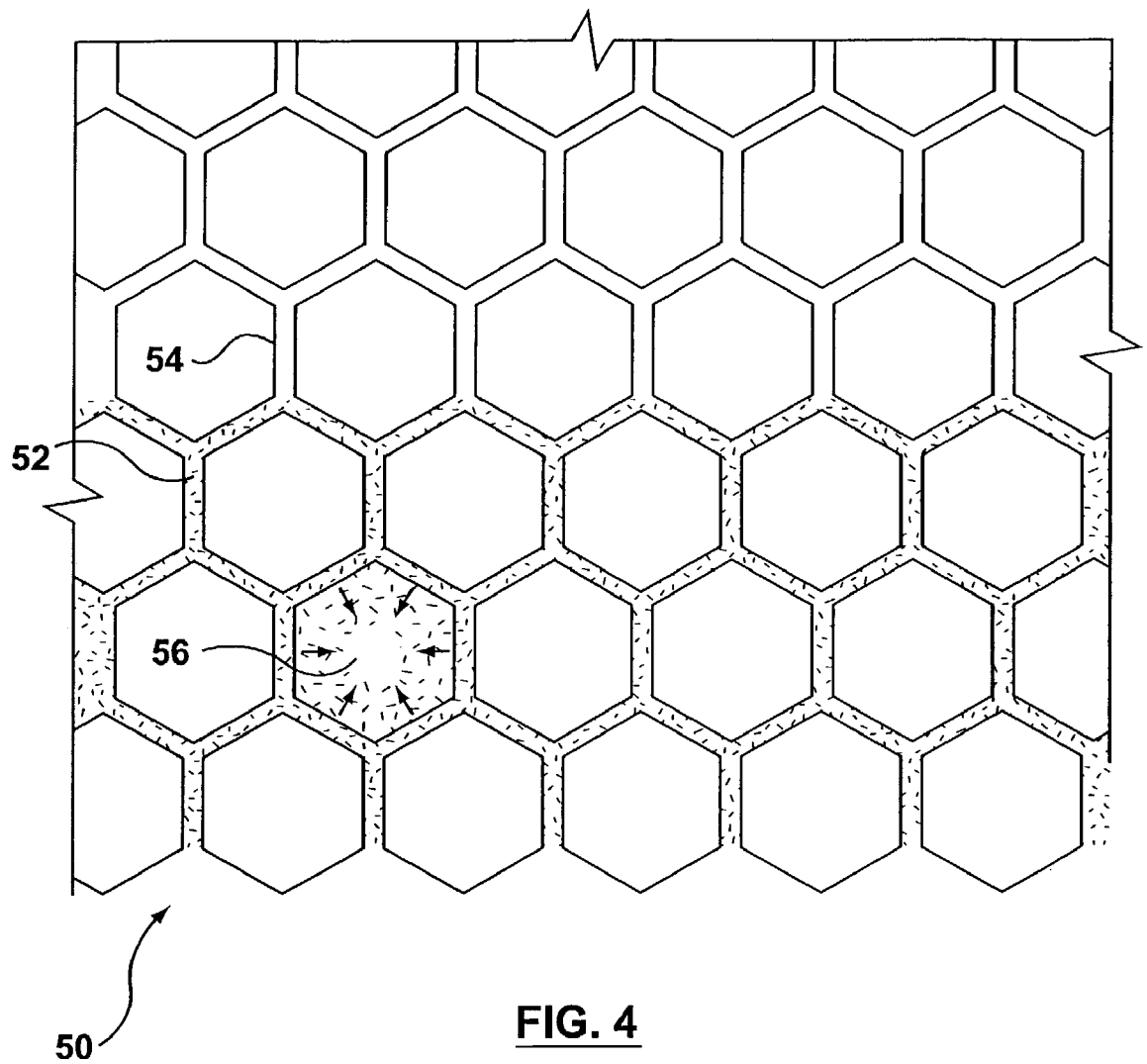
FIG. 4 is a top view of an antimicrobial paper towel.

FIG. 4 illustrates schematically a paper towel 50 on which the antimicrobial composition 52 has been flexographically printed in a honeycomb pattern. Although the composition 52 is initially applied to the honeycomb walls 54, there may be a capillary effect which is dependent on the type of substrate used. This effect allows the antimicrobial composition to disperse into the cores 56. It is clearly apparent that various other printing patterns can be used and that the amount of dispersion depends on both the printing pattern and the type of paper substrate used.

Figure 5:
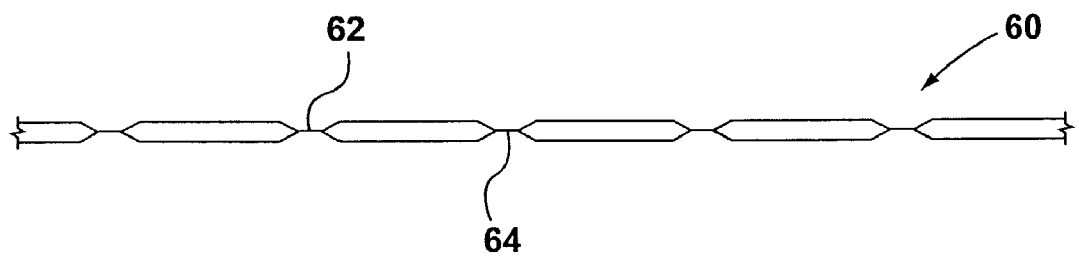
FIG. 5 is a cross-sectional view of a paper towel.

FIG. 5 is a schematic cross-section through a paper towel 60 that has been printed on both sides 62, 64 with an antimicrobial composition. The printing may or may not result in compression of the paper product.

In a preferred method of the present invention, a stock solution is prepared which has an antimicrobial active concentration of 50% by weight. The stock solution can be stored and used in the preparation of different formulations of antibacterial compositions.

Table 1 illustrates a few examples of various formulations of antimicrobial compositions that were prepared and tested in a flexographic printing system.

Table 2 illustrates some examples of formulations of antimicrobial compositions that were prepared and tested using a roto gravure printing system.

The following abbreviations are used in the tables:
OX=OPP=ortho-phenylphenol (e.g. Preventol O Extra from Bayer AG)
ONX=SOPP=sodium ortho-phenylphenolate (e.g. Preventol ON Extra from Bayer AG)
PG=propylene glycol (e.g. USP grade from Ashland Chemical)
$PEG_{abc}$=polyethylene glycol where a, b, c represent integers for the average gram molecular weight of the distribution (e.g. Carbowax from Union Carbide)
PVOH=polyvinyl alcohol (e.g. Vinol 205 crystals by Air Products and Chemicals Inc.)
PVOH 8%=Vinol 205 used as 8% by weight of solution in process water
Cetylol=cetyl alcohol powder (e.g. Kalcol 6098 by KAO Corporation)
APS=stearyl ether with propylene oxide (e.g. Varionic APS from Goldschmidt Chemical Corp.)
Surf 365=ethoxylated Castor Oil (e.g. Surfactol 365 from CasChem Inc.)
nPrOH=normal propanol or propyl alcohol In both tables, the values for the various components are presented as a percent by weight ratio. In a preferred embodiment, the antimicrobial composition comprises 30 to 45% by weight of a phenol-derived antimicrobial agent, 30 to 45% by weight of a solvent, and 10 to 40% by weight of a carrier.

More preferably, the composition comprises 35 to 42% by weight of 2-phenylphenol; 35 to 42% by weight of propylene glycol; and 16 to 30% by weight of a polyethylene glycol.

Referring to the rows labeled "% ADD-ON" on each table, it can be seen that the various antimicrobial compositions were effectively loaded onto the substrate. The extent of loading (% ADD-ON) was calculated using the following formula:

$$\frac{\text{Net Weight of Liquid Mixture Coating}}{\text{Net weight of Plain Paper Used}} \times 100\%$$

FORMULAE FOR ANTIBACTERIAL LIQUIDS USED FOR COATING PAPER BY GRAVURE PRESS

| Ingredient | TRIAL: | | | | | |
|---|---|---|---|---|---|---|
| | CT-17 | CT-18 | CT-19 | CT-20 | CT-21 | CT-22 |
| | (Proportion as Percentage by Weight of Mixture) | | | | | |
| OPP = OX | 32.26% | Same as Formula CT-17 | ø | 39.86% | 29.66% | 25.06% |
| SOPP = ONX | ø | | ø | ø | ø | ø |
| PG | 32.26% | | ø | 39.86% | 29.66% | 40.56% |
| PEG 400 | 32.09% | | ø | ø | ø | ø |
| PEG 600 | ø | | 98.0% | 19.88% | 39.86% | 33.68% |
| PEG 3350 | 0.16% | | ø | ø | ø | ø |
| PEG 8000 | ø | | 2.0% | 0.41% | 0.81% | 0.69% |
| PVOH 8% | 2.67% | | ø | ø | ø | ø |
| Cetylol | 0.56% | | ø | ø | ø | ø |
| TOTALS: | 100.0% | | 100.0% | 100.01% | 99.99% | 99.99% |
| ADD-ON (%) | 6.57 | 3.54 | 4.22 | 11.38 | 21.89 | 2.58 |
| SPEED (FPM) | 500 | 1500 | 500 | 500 | 500 | 1500 |

FORMULAE FOR ANTIBACTERIAL LIQUIDS USED FOR COATING PAPER BY FLEXOGRAPHY

| | TRIAL: | | | | | | | | | | | | |
|---|---|---|---|---|---|---|---|---|---|---|---|---|---|
| | FX-1 | FX-2 | FX-3 | FX-4 | FX-5 | FX-6 | FX-7 | FX-8 | FX-23 | FX-24 | FX-25 | FX-26 | MS-1 |
| OPP = OX | ø | 18.64 | 14.79 | 13.31 | 37.93 | 23.50 | 11.74 | 9.40 | ø | ø | 9.67 | 7.44 | 19.49 |
| SOPP = ONX | ø | ø | ø | ø | ø | ø | ø | ø | 15.09 | 7.51 | 7.53 | 10.84 | ø |
| PG | ø | 18.64 | 14.79 | 13.32 | 37.93 | 23.50 | 11.74 | 9.40 | ø | ø | 40.07 | 14.86 | 49.62 |
| PEG 200 | 100.0 | 62.73 | 49.79 | 44.82 | 24.14 | 14.96 | 52.48 | 42.02 | ø | 50.24 | 35.19 | 56.02 | PEG 400 = 30.89 |
| APS | ø | ø | 20.63 | 28.55 | ø | ø | ø | ø | ø | ø | ø | ø | ø |
| SURF 365 | ø | ø | ø | ø | ø | 38.04 | 24.04 | 19.25 | ø | ø | ø | ø | ø |
| NPrOH | ø | ø | ø | ø | ø | ø | ø | 19.93 | ø | ø | ø | ø | ø |
| DIW | ø | ø | ø | ø | ø | ø | ø | ø | 84.91 | 42.25 | 7.54 | 10.84 | ø |
| TOTALS | 100 | 100.01 | 100.00 | 100.00 | 100.00 | 100.00 | 100.00 | 100.00 | 100.00 | 100.00 | 100.00 | 100.00 | 100.00 |
| ADD-ON (%) | 3.90 | 3.36 | 3.02 | 3.27 | 4.71 | 3.25 | 2.11 | 3.27 | 4.84 | 5.46 | 4.50 | 3.33 | — |
| SPEED (FPM) | 186 | 600 | 604 | 600 | 600 | 500 | 600 | 600 | 250 | 400 | 425 | 460 | — |
| VISCOSITY | — | 20.25 | 24.5 | 27.2 | 27.6 | 36.0 | 19.1 | 11.6 | — | — | 14.2 | 14.5 | — |

Referring to Table I, it can be seen that the FX-5 run in particular had a good deposition of the ortho-phenyphenol (OPP).

Using a gravure press as indicated in Table 2, the CT-20 and CT-21 runs demonstrated a high degree of loading of the antimicrobial active agent onto the substrate.

To determine the actual content of actives (% actives) applied onto the paper substrate, the following calculation can be done:

$$\frac{\%\ \text{Active Component} \times \%\ \text{Add-On}}{100\%}$$

The antimicrobial efficacy of the finished product can be assessed in several ways.

For example, a small square can be cut from the antimicrobial towel and placed in a bag with sterile water. An aliquot of a bacterial culture is added and at several time intervals, a sample is removed and a plate count is performed. The bacterial counts in the paper towel treated samples are compared to a control sample that was cultured in the absence of treated paper towel.

In one aspect of the invention a paper product that is biocidal to a variety of microorganisms is provided. Samples of paper from flexographic (FX) and rotogravure (CT) runs were taken and tested for their biocidal effect against *Salmonella choleraesuis, Escherichia coli* and *Staphylococcus aureus* as described more fully in Example 3 below. Culture samples were taken after exposure to the paper for 15 sec, 1 min and 5 min. Table 3 below indicates the $\log_{10}$ reduction factor for a *Salmonella choleraesuis* culture.

TABLE 3

| | Time (minutes) | | |
|---|---|---|---|
| PRODUCT | 0.2 | 1 | 5 |
| FX-2 | 0.17 | 0.22 | 0.90 |
| FX-5 | 0.51 | 0.99 | 4.5 |
| CT-20 | 1.35 | 3.19 | 3.74 |
| CT-21 | 1.25 | 1.57 | 2.36 |

In another embodiment, an anti-*E. coli* paper product is provided. The efficacy against *E. coli* was assessed using the same protocol as described above and in Example 3. These results are shown in Table 4 below.

TABLE 4

| | Time (minutes) | | |
|---|---|---|---|
| PRODUCT | 0.2 | 1 | 5 |
| FX-2 | 0.01 | 0.03 | 0.72 |
| FX-5 | 0.50 | 0.86 | 0.97 |
| CT-21 | 0.61 | 0.86 | 0.96 |

In yet another embodiment, a paper product effective against *Staphylococcus aureus* is provided. The efficacy results are shown in Table 5 below.

TABLE 5

| | Time (minutes) | | |
|---|---|---|---|
| PRODUCT | 0.2 | 1 | 5 |
| FX-2 | 0.00 | 0.01 | 0.40 |
| FX-5 | 0.07 | 2.59 | 2.81 |
| CT-21 | 0.00 | 0.01 | 2.11 |

The results indicate that all of the samples of antimicrobial paper had antimicrobial activity against *Salmonella choleraesus, Escherichia coli* and *Staphylococcus aureus* and that the effect increased with the exposure time. The paper products of the present invention have also been shown to be effective against the organism *Serratia marcescens* as described in Example 4 below. The results indicate that the paper products are effective against a variety of both gram positive and gram negative organisms.

It should be noted that the initial innoculum count for each of the organisms was very high, approximately $85 \times 10^5$. Thus, this is a very onerous test for the paper and even a small $\log_{10}$ reduction factor represents a significant biocidal and/or biostatic effect. It is clearly apparent that a much greater $\log_{10}$ reduction factor can be achieved using a lower bacterial load, in the range of that which would be expected on hands that had just been washed.

It has also been shown that the product is stable. In a similar assay using *Salmonella choleraesius*, the efficacy of an FX-5 sample taken two weeks after the run was compared to the efficacy of a sample from the same run after storage for approximately eight months. The two week sample showed a $Log_{10}$ decrease in CFU/ml of 0.51, 0.99 and 4.5 at 15 sec., 60 sec. and 300 sec. respectively. The eight month sample showed a $Log_{10}$ decrease in CFU/ml of 0.61, 1.73 and 3.43 at 15, 60 and 300 seconds, respectively. It is clearly apparent that long-term storage did not significantly affect the antimicrobial activity of the product.

A comparison of the results obtained for FX-2 and FX-5 suggests that the antimicrobial efficacy of the sample correlates with the % ADD-ON of the active agent.

Figure 6:
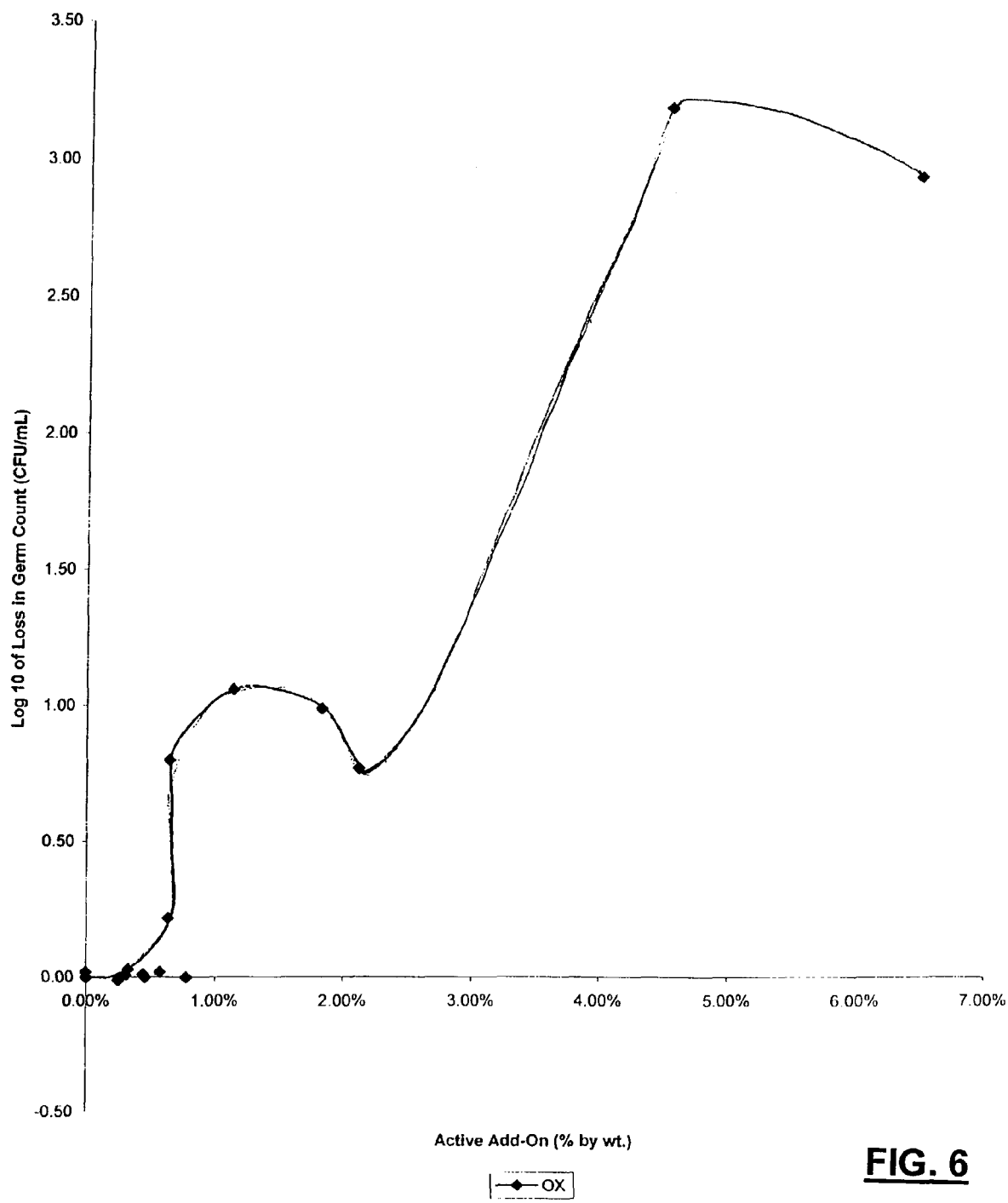
FIG. 6 is a graph indicating antimicrobial efficacy at 60 seconds.

FIGS. 6 and 7 further illustrate the effect of the % Add-On on the ability to kill Salmonella in sixty seconds and five minutes, respectively.

The antimicrobial activity of the product can also be assessed by preparing a bacterial culture on a growth medium and placing a sample of the paper product on/in the medium. The biocidal and/or biostatic effects can be assessed visually by observing a ring of non-growth around the paper.

Another way to test the efficacy of the paper product is to incubate a bacterial culture in the presence of a sample of antimicrobial paper or a sample of control paper. After a pre-determined incubation time, an aliquot is removed and a bacterial count is done.

Alternatively the paper product can be rinsed and the run-off tested for activity. Standard microbiological assays for biocidal/biostatic activity are well know to those skilled in the art and can be used to determine the antimicrobial activity of the product.

The anti-viral and anti-fungal properties can be assessed in similar ways. For example, viral infectivity of cells in the presence of the paper product can be determined. Generally, the antimicrobial properties of the treated paper product can be assessed using a variety of standard microbiological assays.

The in vivo efficacy of the products can also be determined. For example, the bacterial load on an individual's hands can be assessed before and after drying the hands with a paper towel treated according to the present invention. One hand is dried with an antimicrobial paper towel and the other hand is dried with a regular paper towel. The hands are then rinsed with sterile water and a bacterial count is done.

The residual effect on re-contamination can also be assessed. For example, at a time after drying, treated and untreated hands can be rinsed with sterile water and samples of the rinsate can be plated to determine the bacterial count. Alternatively, the hands can be directly contacted with a microorganism growth medium.

The in vivo efficacy can also be demonstrated using different types of assays well known to those skilled in the art. In one such assay, a surface is coated with a bacterial solution. The surface is then dried with an antimicrobial paper product of the present invention. The surface is then rinsed and the number of residual bacteria in the rinsate is determined. The effect of the paper product can be assessed by determining the decrease in bacteria.

The results discussed herein demonstrate that antimicrobial paper towels prepared according to the present invention are effective for infection control. The antimicrobial paper products of the present invention are highly effective against a wide variety of microorganisms.

The antimicrobial paper products of the present invention are useful in a variety of ways. The antimicrobial paper product is preferably a paper hand towel.

In practice, a person washes their hands and then uses the antimicrobial paper towel to dry them. The friction generated by the engagement of the hands and the towel transfers the antimicrobial agent to the person's hands. The water on the person's hands may also act to liberate and activate the antimicrobial ingredient from the dry paper towel. The hands become sanitized as they are dried. In addition to the pre-existing microorganisms on the hands, undesirable microbes in the tap water are also affected. Antimicrobial paper hand towels are of particular value in environments such as food handling stations and hospital settings. Because the antimicrobial is not rinsed off the hands after drying, there is an ongoing residual antimicrobial effect. Antimicrobial paper towels may be provided as a rolled product, a folded sheet product or a pre-packaged single use product.

In another aspect of the invention, the antimicrobial paper product is a facial tissue. When a person uses the tissue to, for example, blow their nose, the microbial load on the tissue is decreased before it is disposed of, thereby reducing the spread of germs. In addition, the antimicrobial ingredient is active in the dry state and may be passed onto the hands, further reducing the spread of disease.

The antimicrobial paper product may comprise a kitchen towel. The towel can be dampened and used to clean surfaces. Alternatively, a dry towel can be used to dry surfaces that were wet with water and provide a residual antimicrobial effect.

The release of the antimicrobial from the antimicrobial paper product in the presence of an exogenous fluid is also a useful feature for antimicrobial toilet paper and other personal hygiene products.

The paper products of the present invention may include, in addition to the antimicrobial, other additives. For example, a skin protectant or moisturizer can be included. Additives such as stabilizers, chemical additives, astringents, binders, fragrances, emollients and a wide variety of other compounds, as will be apparent to those skilled in the art, can also be included. The paper product may comprise more than one type of antimicrobial. For example, a paper towel could be impregnated with an anti-bacterial and an anti-fungal. Various combinations of additives are contemplated.

The paper products of the present invention provide significant advantages over current antimicrobial wipes. The products are essentially dry and therefore easy to store. The antimicrobial is released from the paper fibres in the presence of water. The products are stable since the antimicrobial active agent has a long shelf life, especially in the dry form. The high degree of specialty packaging that is necessary for wet wipes is not required for the present invention since there is no need, or even desire, to keep the product moist. In addition, the products of the present invention do not contain high amounts of alcohol or other agents which can irritate the skin.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Methods of papermaking, chemistry and microbiology referred to but not explicitly described in this disclosure and examples are well known to those skilled in the art.

EXAMPLES

The examples are provided for purposes of illustration. Although specific terms have been employed herein, such terms are intended in a descriptive sense and not for purposes of limitation.

Example 1

Preparation of a Stock Antimicrobial Composition

To prepare a 2-phenylphenol stock mix, Preventol O Extra™ was purchased from Bayer. A stock of propylene glycol was heated slowly over one hour to a temperature of approximately 60° C. Preventol, in the form of crystalline flakes, was added slowly in four equal aliquots for a final concentration of 50% by weight of the stock solution. The solution was mixed for 15 minutes and the heating was stopped. After approximately 15 minutes more, the stock solution was transferred to a drum. The stock solution can be stored and used in the preparation of different formulations of antibacterial compositions.

Example 2

Preparation of an Antimicrobial Paper Product

A stock solution comprising equal parts by weight of 2-phenylphenol and polyglycol was prepared. Approximately 25% by weight of PEG 200 was added. The resulting composition had a viscosity of approximately 200 cP or mPs. The composition was applied to a paper towel web using a flexographic printing technique with the web moving at a speed of approximately 600 FPM.

Example 3

Antimicrobial Efficacy of Flexographic Printed Towels

Two examples of antimicrobial paper towel were tested for their efficacy against *Salmonella choleraesuis* (ATCC 14028), *Escherichia coli* (ATCC 8739) and *Staphylococcus aureus* (ATCC 6538). Samples from two flexographic runs, termed FX-2 and FX-5, were cut into 10 cm×10 cm squares (100 cm$^2$). The two samples, FX-2 and FX-5 were printed with different antimicrobial compositions as defined in Table 1. The pieces of paper were placed in a sterile bag and 1 ml. of sterile water was added to each. A 0.5 ml. aliquot of a 24-hour culture of one of the test organisms was then added. After contact times of 15 sec., 1 min., and 5 min., 10 mls of Letheen Broth was added per each piece of paper and bag was agitated. A sample was then taken and a plate count assay was set up in duplicate for each piece. The plates were incubated at 30-35° C. for 48 hours. The initial inoculum count for each of the organisms is as follows:

| | |
|---|---|
| S. choleraesuis: | $88 \times 10^5$ |
| E. coli: | $79 \times 10^5$ |
| S. aureus | $90 \times 10^5$ |

Media controls comprising TSA, Letheen Broth or normal saline did not show any growth.

The efficacy results are shown in the following table.

TABLE 6

| Organism | FX-2 | FX-5 |
|---|---|---|
| *S. choleraesuis* | | |
| 15 sec. | $59 \times 10^5$ | $27 \times 10^5$ |
| 1 min. | $53 \times 10^5$ | $91 \times 10^4$ |
| 5 min. | $11 \times 10^5$ | $28 \times 10^1$ |
| *E. coli* | | |
| 15 sec. | $78 \times 10^5$ | $25 \times 10^5$ |
| 1 min. | $79 \times 10^5$ | $11 \times 10^5$ |
| 5 min. | $15 \times 10^5$ | $85 \times 10^4$ |
| *S. aureus* | | |
| 15 sec. | $89 \times 10^5$ | $76 \times 10^5$ |
| 1 min. | $88 \times 10^5$ | $23 \times 10^3$ |
| 5 min. | $36 \times 10^5$ | $14 \times 10^3$ |

These results indicate that the antimicrobial paper towels are effective against both gram-positive and gram-negative bacteria.

Example 4

Efficacy Against *Serratia marcescens*

One flexograph sample and two rotogravure samples were tested for antimicrobial efficacy against the microorganism, *Serratia marcescens* (ATCC14756). The compositions used for the printing are outlined in Table 2 above. Samples FX-5, CT21 and CT22 were cut in 100 cm$^2$ squares and the squares were placed in sterile bags. One milliliter of either sterile reagent-grade (deionized and purified by Millipore unit) water or sterile tap water (drinking water from Orangeville, Ontario) was added to each sample. An aliquot of 0.5 ml of the test organism was then added. After 15 sec, 1 min and 5 min, 10 ml of Letheen Broth was added to each bag and agitated. Plate counts were then performed in duplicate as described above.

The initial inoculum count was 72×10$^7$. The results of the assay are shown in Table 7 as follows.

TABLE 7

| Diluent | FX-5 | CT-22 | CT-21 |
|---|---|---|---|
| Millipore water | | | |
| 15 sec. | $15 \times 10^7$ | $65 \times 10^7$ | $24 \times 10^7$ |
| 1 min. | $25 \times 10^6$ | $62 \times 10^7$ | $20 \times 10^7$ |
| 5 min. | $21 \times 10^6$ | $23 \times 10^7$ | $11 \times 10^7$ |
| City water | | | |
| 15 sec. | $12 \times 10^7$ | $31 \times 10^6$ | $26 \times 10^7$ |
| 1 min. | $46 \times 10^6$ | $27 \times 10^7$ | $21 \times 10^7$ |
| 5 min. | $30 \times 10^6$ | $15 \times 10^7$ | $14 \times 10^7$ |

These results indicate that different samples of paper towel are effective anti-bacterial agents.

Example 5

In Vivo Assay for Antimicrobial Activity

To test the in vivo efficacy of a hand towel according to the present invention, an aliquot of a bacterial culture is applied to an individual's hands. The hands are washed and then dried using a regular paper towel or an antimicrobial paper towel of the present invention. The hands are then rinsed with sterile water and a bacterial count is performed on the rinse.

Although preferred embodiments of the invention have been described herein in detail, it will be understood by those skilled in the art that variations made be made thereto without departing from the spirit of the invention or the scope of the appended claims.

I claim:

1. A dry paper towel comprising a substrate and a single antimicrobial composition disposed on said substrate, wherein said composition is surfactant-free and said composition comprises a hydrophilic solvent in which is dispersed only a single antimicrobial active agent, wherein said antimicrobial active agent is 2-phenylphenol and wherein the paper towel exhibits a log 10 decrease in CFU/ml of at least about 0.1 for an exposure of 15 minutes.

2. The paper towel according to claim 1, wherein the hydrophilic solvent is selected from the group consisting of methanol, ethanol, ethylene glycol, isopropanol, polyglycol, propylene glycol and mixtures thereof.

3. The paper towel according to claim 1, wherein the antimicrobial composition comprises from about 5% to about 95% by weight of the antimicrobial active agent.

4. The paper towel according to claim 3, wherein the antimicrobial composition comprises from about 5% to about 50% by weight of the antimicrobial active agent.

5. The paper towel according to claim 2, wherein the solvent comprises propylene glycol.

6. The paper towel according to claim 1, wherein the antimicrobial composition further comprises a carrier.

7. The paper towel according to claim 6 wherein the carrier comprises polyethylene glycol and the antimicrobial composition comprises about 16% to about 30% of the carrier by weight.

8. The paper towel according to claim 7, wherein the carrier is selected from the group consisting of PEG200, PEG400, PEG600, PEG3350, PEG8000 and mixtures thereof.

9. The paper towel according to claim 1, wherein the antimicrobial composition further comprises an additional component selected from the group comprising consisting of an alcohol, an emollient, a fragrance and combinations thereof.

10. A rolled product comprising the paper towel according to claim 1.

11. A folded sheet product comprising the paper towel according to claim 1.

12. A pre-packaged, single use product comprising the paper towel according to claim 1.

13. A paper product that exhibits a log 10 decrease in CFU/ml of at least about 0.1 for an exposure of 15 minutes, said paper product comprising a substrate selected from the group consisting of a paper hand towel, a napkin, facial tissue, toilet paper and household paper towels and a single antimicrobial composition wherein said antimicrobial composition is surfactant-free and comprises 30 to 45% by weight of a hydrophilic anhydrous solvent in which is dispersed 30 to 45% by weight of only a single antimicrobial agent, wherein said agent is a phenol-based antimicrobial agent, and 10 to 40% by weight of a carrier.

14. The paper product according to claim 13, wherein the antimicrobial composition comprises:
  i) 35 to 42% by weight of 2-phenylphenol;
  ii) 35 to 42% by weight of propylene glycol; and
  iii) 16 to 30% by weight of a polyethylene glycol.

15. A dry paper towel comprising a substrate and a single antimicrobial composition disposed on said substrate, wherein said composition is biodegradable and surfactant-free, said composition comprising a hydrophilic solvent in which is dispersed a phenol-based antimicrobial active agent, wherein the paper towel exhibits a log 10 decrease in CFU/ml of at least about 0.1 for an exposure of 15 minutes.

16. The paper product according to claim 13, wherein the phenol-based antimicrobial agent is selected from the group consisting of 2-phenylphenol, sodium-2-phenylphenolate, hexachlorophene, chlorhexidine or diphenyl ethers.

17. The paper product according to claim 15, wherein the phenol-based antimicrobial agent is selected from the group consisting of 2-phenylphenol, sodium-2-phenylphenolate, hexachlorophene, chlorhexidine or diphenyl ethers.

18. A method of preparing an antimicrobial paper product as defined in claim 13, said method comprising applying to the paper substrate the surfactant-free antimicrobial composition.

19. The method of claim 18, wherein said composition is applied using a process selected from the group consisting of spraying, flexographic printing and roto gravure printing.

20. The method of claim 18, wherein the paper product is a paper towel.

* * * * *